(12) United States Patent
Ström

(10) Patent No.: US 6,240,920 B1
(45) Date of Patent: Jun. 5, 2001

(54) METHOD FOR DETERMINING A PARAMETER RELATED TO SPONTANEOUS BREATHING EFFORTS BY A SUBJECT, AND BREATHING-ASSIST APPARATUS OPERATING IN ACCORDANCE WITH THE METHOD

(75) Inventor: Christer Ström, Pitea (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/287,315

(22) Filed: Apr. 7, 1999

(30) Foreign Application Priority Data

Apr. 23, 1998 (SE) .................................................. 9801427

(51) Int. Cl.$^7$ .................................................. A61M 16/00
(52) U.S. Cl. ................ 128/204.23; 128/200.24
(58) Field of Search ........... 128/204.18, 204.21–204.23, 128/204.26, 205.24, 200.24

(56) References Cited

U.S. PATENT DOCUMENTS

| 5,535,738 | * | 7/1996 | Estes et al. | ...................... 128/204.21 |
| 5,743,253 | * | 4/1998 | Castor et al. | .................... 128/200.24 |
| 5,752,506 | * | 5/1998 | Richardson | ...................... 128/204.21 |
| 5,752,509 | * | 5/1998 | Lachmann et al. | ............. 128/204.23 |
| 5,771,897 | * | 6/1998 | Zufrin | ................................. 128/670 |
| 5,878,744 | * | 3/1999 | Pfeiffer | ............................ 128/204.23 |
| 5,884,622 | * | 3/1999 | Younes | ............................ 128/204.23 |
| 5,915,381 | * | 6/1999 | Nord | ................................ 128/204.23 |
| 5,931,162 | * | 8/1999 | Christian | ......................... 128/204.23 |

FOREIGN PATENT DOCUMENTS

| 4432219 C1 | * | 11/1996 | (DE) | ................................ 128/204.23 |
| 0402951 A3 | * | 12/1990 | (EP) | ................................ 128/204.23 |

* cited by examiner

*Primary Examiner*—Aaron J. Lewis
*Assistant Examiner*—Teena Mitchell
(74) *Attorney, Agent, or Firm*—Schiff Hardin & Waite

(57) ABSTRACT

In a method and apparatus for determining at least one parameter related to a patient's spontaneous attempts at inspiration and/or the patient's respiratory effort in attempts at spontaneous inspiration, a pressure gradient is determined in relation to a known apparatus pressure and time, the pressure gradient being generated by the patient at inspiration, a residual positive pressure in the patient's lungs is determined and an output signal is generated. The output signal can represent determined parameters as well as other related calculated results. The pressure gradient can be extrapolated against residual positive pressure, and both a delay for respiratory assistance and true inspiratory effort can be determined.

15 Claims, 3 Drawing Sheets

METHOD FOR DETERMINING A PARAMETER RELATED TO SPONTANEOUS BREATHING EFFORTS BY A SUBJECT, AND BREATHING-ASSIST APPARATUS OPERATING IN ACCORDANCE WITH THE METHOD

BACKGROUND OF THE INVENTION

1. Field of the Invention

The present invention is directed to a method for determining at least one parameter related to a patient's spontaneous attempts at inspiration and/or the patient's respiratory effort in spontaneous attempts at inspiration, as well as to an apparatus operating according to the method and making use of the parameter to assist breathing in the patient.

2. Description of the Prior Art

In normal, spontaneous inhalation, the respiratory musculature creates negative pressure in the chest cavity, causing air to be drawn down into the lungs. The negative pressure formed in the initial 100 ms of a breath is directly proportional to the respiratory incentive generated in the respiratory center of the medulla oblongata. The respiratory incentive reflects, in turn, the body's need for e.g. oxygen. Accordingly, a large respiratory incentive results in a deep breath, e.g. during heavy physical exertion when the body needs a large amount of oxygen. A normal value for the respiratory incentive is about a 2 cmH$_2$O drop in pressure in the first 100 ms. During expiration, the musculature relaxes, and air is expelled from the lungs.

In injuries and illness, a patient's ability to breathe may be so compromised that supplementary respiratory assistance must be provided by a breathing apparatus, usually a ventilator. This may also be the case when a patient's ability to breathe is suppressed, e.g. during anaesthesia.

The term "patient" as used herein refers, in principle, to all creatures which breathe with lungs, but to humans and domesticated animals in particular.

Ventilators are equipped with triggering systems, which induce an inspiration (inspiratory phase) whenever an attempt by the patient to inhale is detected. Triggering systems can be based on the measurement of pressure, the patient then being required to generate a drop in pressure sufficient to trigger the ventilator, or on the measurement of flow, the patient then being required to generate a gas flow sufficient to trigger the ventilator. The gas flow generated naturally depends on the negative pressure the patient is able to produce. Combinations of pressure measurement and flow measurement are also used.

The ventilator supplies breathing gas at the flow and pressure set by the physician for each patient. For example, the physician sets the apparatus pressure to which the patient is subjected at the end of an expiration (PEEP—Positive End Expiratory Pressure or, less commonly, NEEP—Negative End Expiratory Pressure). PEEP refers to a positive pressure in relation to the surroundings and can therefore range from 0 cmH$_2$O on up. The physician also selects the ratio between inspiratory duration and expiratory duration.

In other words, the patient must make some inspiratory effort in order to trigger the ventilator into delivering a flow of gas. If a patient is unable to make this effort, the ventilator must, in principle, exercise complete control over the patient's breathing. Even if this is essential to the survival of many patients, it could simultaneously contribute to a weakening or, at worst, atrophy of the patient's respiratory musculature. This leads, in turn, to prolonged recovery times and a heavier burden on treatment facilities (both in terms of costs and bed occupancy).

Effective triggering therefore could result in more rapid recovery and weaning off respiratory assistance for the patient. When a magnitude for the respiratory incentive is selected at which a large inspiratory incentive causes more breathing gas to be supplied, respiratory assistance can be better tailored to the patient's needs.

One problem in this context concerns the presence of residual positive pressure inside the lungs. In the present application, this residual positive pressure is designated Auto-PEEP. A number of factors can lead to the development of residual positive pressure in the lungs. Some of these factors are physiological, such as flow resistance in the lungs slowing evacuation of some parts of the lungs. Other factors are apparatus-related, such as the ratio between inspiration duration and expiration duration and between respiratory rate and tidal volume.

Auto-PEEP causes the true pressure gradient the patient needs to overcome in order to trigger the ventilator to exceed the value anticipated at the prevailing ventilator settings. The effort the patient must make increases, and the delivery of breathing gas is delayed.

Therefore, a more reliable way of determining when the patient starts an inspiration is needed so respiration can be facilitated in the best way possible.

SUMMARY OF THE INVENTION

An object of the present invention is to provide a method making it possible to determine the patient's true circumstances in relation to her/his inspiratory effort/attempts at inspiration.

Another object of the invention is to provide a method making it possible to determine the patient's anticipated attempts at inspiration.

Another object of the invention is to provide a method making possible improved determination of the patient's inspiratory incentive.

A further object of the invention is to provide a method making possible better determination of the patient's inspiratory effort.

Another object of the invention is to provide a breathing apparatus designed for improved detection of the patient's inspiratory effort/attempts at inspiration.

The above objects are achieved in accordance with the invention in a first embodiment of a method for determining at least one parameter related to a patient's spontaneous attempts at inspiration and/or the patient's respiratory effort in spontaneous attempts at inspiration, wherein a pressure gradient is determined relative to a known apparatus pressure and time, the pressure gradient being generated by the patient upon inspiration, wherein a residual positive pressure in the patient's lungs is determined, and wherein a signal is generated dependent at least in part on the residual positive pressure in the patient's lungs.

A number of advantages and various types of information can be obtained when the pressure gradient generated by the patient in inspiration and residual positive pressure in the lungs are determined. A graphic depiction of the determined values can be displayed on a screen on the ventilator or on a separate monitor. When such a graphic display of true conditions is available, the physician is able to assess the true respiratory effort the patient needs to make as well as the delay in the ventilator's response. The physician can then decide whether the true conditions warrant any changes in the patient's treatment.

The delay and respiratory effort also can be calculated by first extrapolating the pressure gradient relative to the level of Auto-PEEP.

The above objects are also achieved in a further embodiment of the inventive method wherein an expiratory curve is determined for one breathing cycle, and signal components are extracted from the expiratory curve which are related to an attempt at inspiration by the patient. A signal is then generated dependent at least in part on these signal components.

Determining the patient's expiratory curve, the flow curve in 10 particular, makes it possible to extract information on conditions in the lung from the curve. Any commenced attempt at inspiration in particular will generate a change in the curve. Analysis of this part of the curve in one or more breaths makes it possible to predict an attempt at inspiration in subsequent breathing cycles. In principle, a real time analysis of the curve can be used for generating a triggering signal when changes in the curve indicate the patient has started an attempt to inhale.

This can also be advantageously combined with the first version of the method described above.

In principle, the above objects are also achieved in a breathing apparatus in accordance with the invention formed by a conventional ventilator equipped with a determination unit performing one or more of the described embodiments of the inventive method.

DESCRIPTION OF THE PREFERRED EMBODIMENTS

Figure 1:
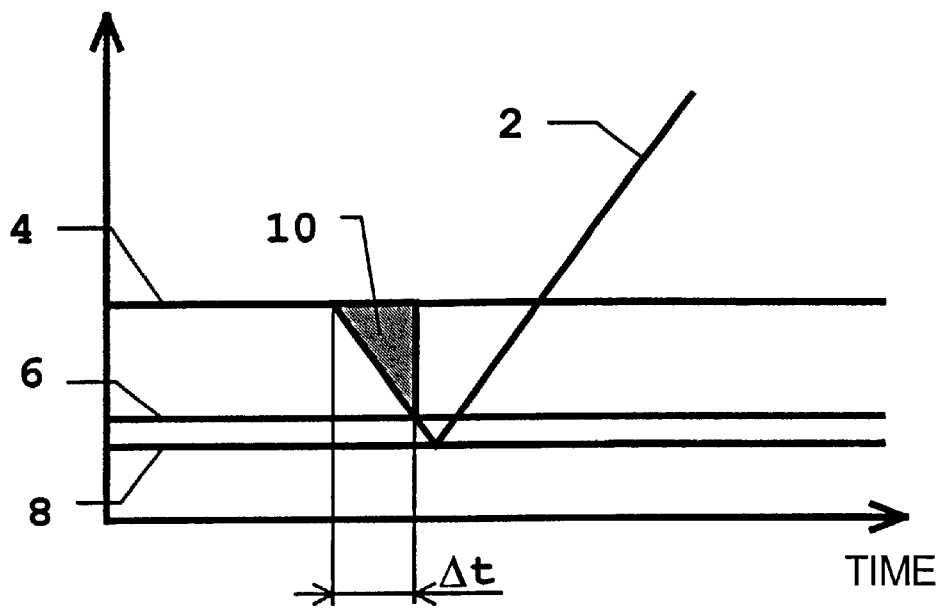
FIG. 1 is a diagram describing a triggering, a triggering delay and a patient's attempt at inspiration.

The diagram in FIG. 1 shows part of a respiratory curve 2 in relation to Auto-PEEP 4, apparatus-PEEP 6 and a triggering level 8. When a patient starts an inspiration, she/he must first overcome the pressure gradient between Auto-PEEP 4 and apparatus-PEEP 6. The difference in pressure between apparatus-PEEP 6 and the triggering level 8 (the descending side of the respiratory curve 2) must thereupon also be overcome before the ventilator supplies respiratory assistance (the rising side of the respiratory curve 2).

The gap between Auto-PEEP 4 and apparatus-PEEP 6 has several consequences. The time required to overcome this gap causes a needless delay $\Delta t$ before respiratory assistance is supplied. The area 10 corresponds to the additional breathing effort the patient must make in order to obtain respiratory assistance. Any attempt to determine the respiratory incentive (see FIG. 2 for additional details on this determination) is also performed with a delay greater than the delay $\Delta t$. The respiratory incentive can be determined in the initial 100 ms of an inspiration, but the delay $\Delta t$ can itself last for 200–250 ms. As a result, determination of the respiratory incentive does not take place until after 250–350 ms. It is then by no means certain that the respiratory incentive determined really corresponds to the patient's true respiratory needs.

Figure 2:
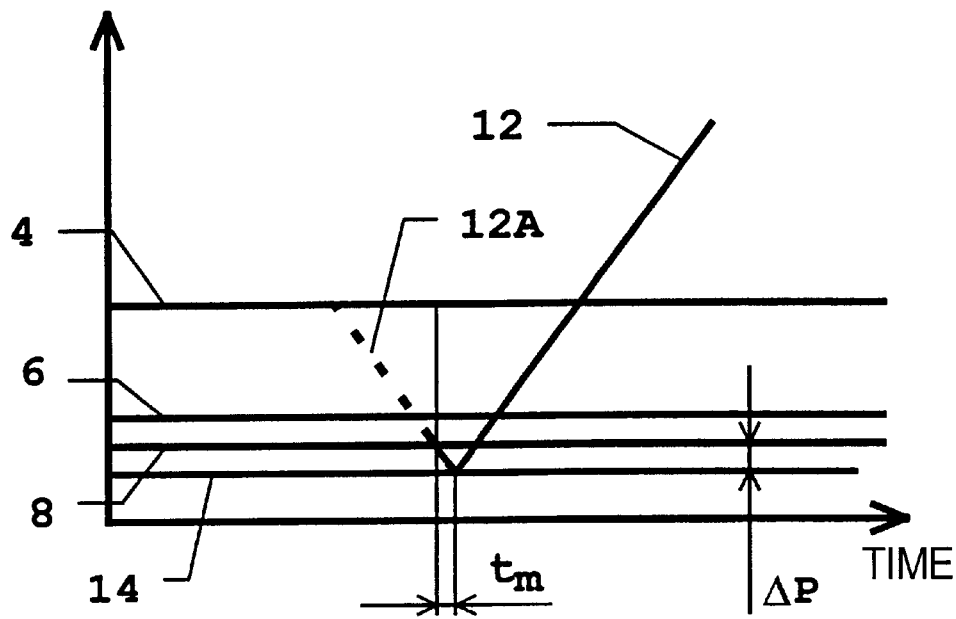
FIG. 2 shows one way to determine a patient's respiratory incentive.

FIG. 2 illustrates the procedure for determining the respiratory incentive. The lines for Auto-PEEP 4, apparatus-PEEP 6 and the triggering level 8 are the same as in FIG. 1. The respiratory curve 12 corresponds to the respiratory curve 2 in FIG. 1.

When the triggering level 8 is reached in a patient's attempt at inhalation, the delivery of respiratory assistance can be delayed for the time tin, e.g. 100 ms. During this period of time, the patient continues to generate negative pressure in her/his lungs, and this negative pressure (the difference between the triggering level 8 and the triggering level 14), designated $\Delta P$, then constitutes the respiratory incentive. The angle for the determined pressure difference $\Delta P$ in relation to the triggering level can be determined and is referred to as the pressure gradient. The intersection with Auto-PEEP 4 can be established by extrapolation, and the delay $\Delta t$ and inspiratory effort 10 in FIG. 1 can be determined.

Extrapolation of the pressure gradient is shown as being linear in FIG. 2, but as is evident from the above description, the respiratory incentive is not necessarily linear throughout this period of time (which can amount to 300–350 ms). Other, non-linear extrapolations can therefore be used in determining the intersection with Auto-PEEP 4. Extrapolation related to the pressure gradient can also be performed. A large pressure gradient (a big difference in the pressure $\Delta P$ during the interval $t_m$) can be subjected to linear extrapolation, whereas a small pressure gradient can be extrapolated with a function yielding a pressure gradient that increases as Auto-PEEP 4 approaches the extrapolation curve 12A.

Figure 3:
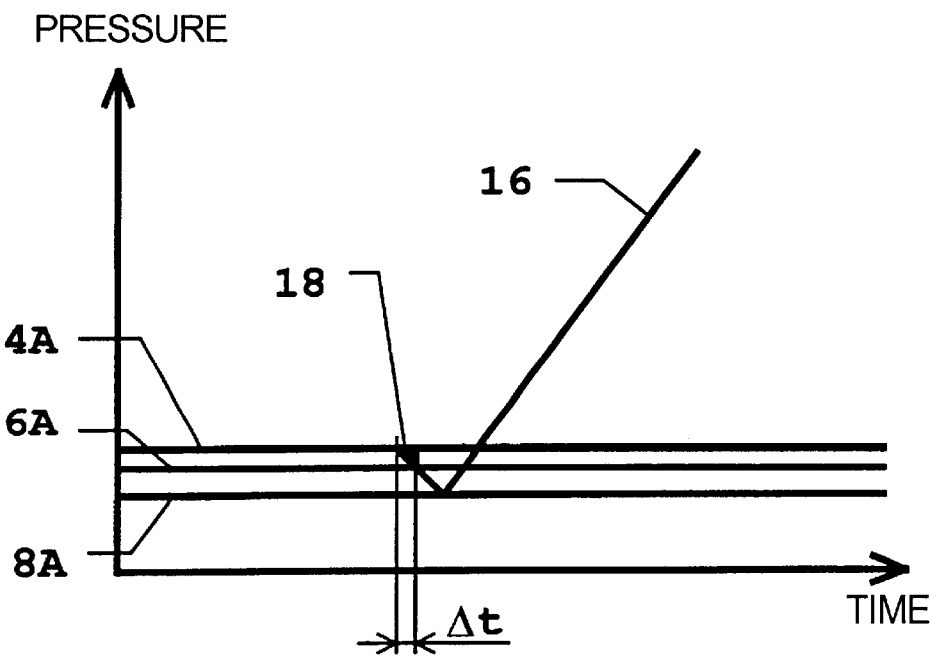
FIG. 3 is a diagram illustrating a tailored Auto-PEEP and apparatus-PEEP.

With appropriate adaptation of respiratory assistance, Auto-PEEP and apparatus-PEEP can be made to approach one another, as illustrated in FIG. 3. FIG. 3 shows Auto-PEEP 4A, apparatus-PEEP 6A and the triggering level 8A with an inspiratory curve 16. FIG. 3 shows that the delay $\Delta t$ before the patient receives breathing assistance is much shorter than in FIG. 1, and additional inspiratory effort 18 is greatly reduced.

Adaptation of respiratory assistance can include one or more of the following changes.

Adaptation of apparatus-PEEP to Auto-PEEP, preferably by allowing apparatus-PEEP to be a percentage (e.g. 70–90%) of Auto-PEEP. This result in improved triggering for the patient and reduced inspiratory effort. The patient's breathing is accordingly facilitated, and Auto-PEEP declines. Continuous monitoring of Auto-PEEP and apparatus-PEEP makes possible a successive reduction in both to a lower level.

An adaptation of the inspiratory and expiratory durations to give the lungs more time to evacuate delivered breathing gas makes it possible to reduce Auto-PEEP. Alternately, the flow curve for delivered breathing gas or tidal volume can be modified to achieve the corresponding effect. Here, modest adaptation may be sufficient to achieve a positive trend, i.e. with a declining Auto-PEEP, thanks to a reduced delay and inspiratory effort.

Figure 4:
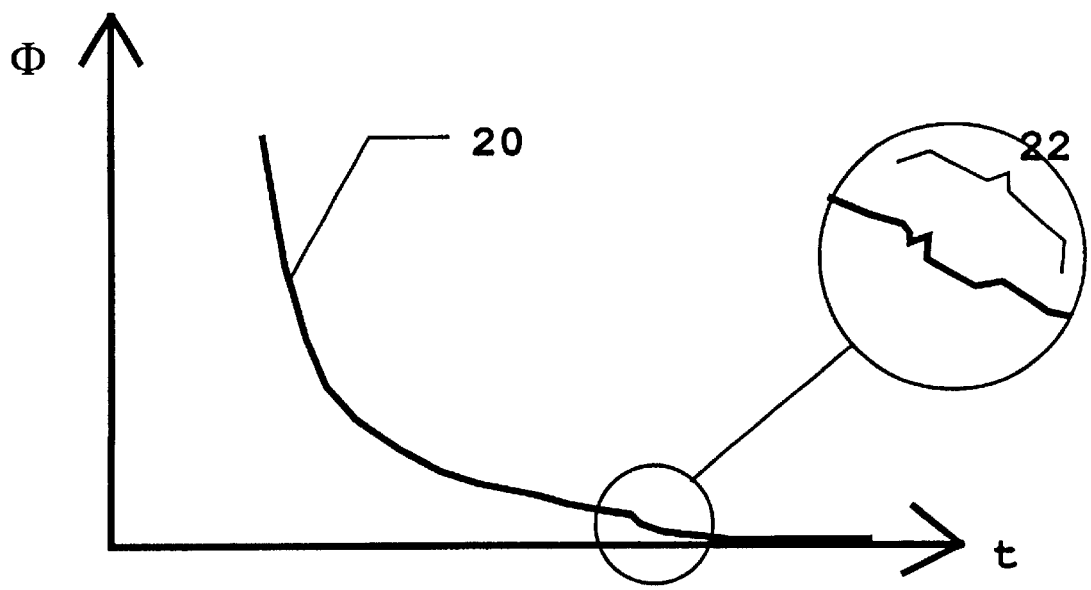
FIG. 4 is a diagram showing an expiratory curve.

FIG. 4 shows an alternative method according to the invention for obtaining essential information related to the patient's attempts at inspiration. The diagram in FIG. 4 shows flow $\phi$ in relation to time t. An expiratory curve 20 designates the way in which breathing gas flows out of the patient's lungs during expiration.

In principle, the expiratory curve 20 designates the way in which the breathing apparatus registers events during apparatus-related expiration. By definition, expiration does not end for the breathing apparatus until the patient triggers a new breath. As is evident from the above, the patient may already have begun an attempt at inspiration at an earlier point in time. This attempt at inspiration therefore occurs, by definition, at the end of the expiratory phase.

An enlarged segment 22 of the expiratory curve 20 shows that fluctuations occur in the flow curve. Some of these fluctuations develop as the result of the patient's commenced attempts at inspiration.

A number of conclusions, preferably based on the corresponding area in two or more respiratory cycles, can be drawn from analysis of this part of the expiratory curve 20. Patient-related fluctuations in particular can then be filtered out.

These fluctuations can then be used for "teaching" the breathing apparatus to identify corresponding variations in subsequent respiratory cycles, such as attempts at inspiration, and trigger breathing assistance before the patient has generated the usual negative pressure and/or change in flow required for triggering.

These fluctuations can also be used for making "predictions", i.e. for calculating an anticipated time at which an attempt at inspiration will be made in the next respiratory cycle. This could be helpful by activating the breathing apparatus at the anticipated time so the breathing apparatus delivers a gas flow enabling triggering to occur with greater sensitively than usual.

Figure 5:
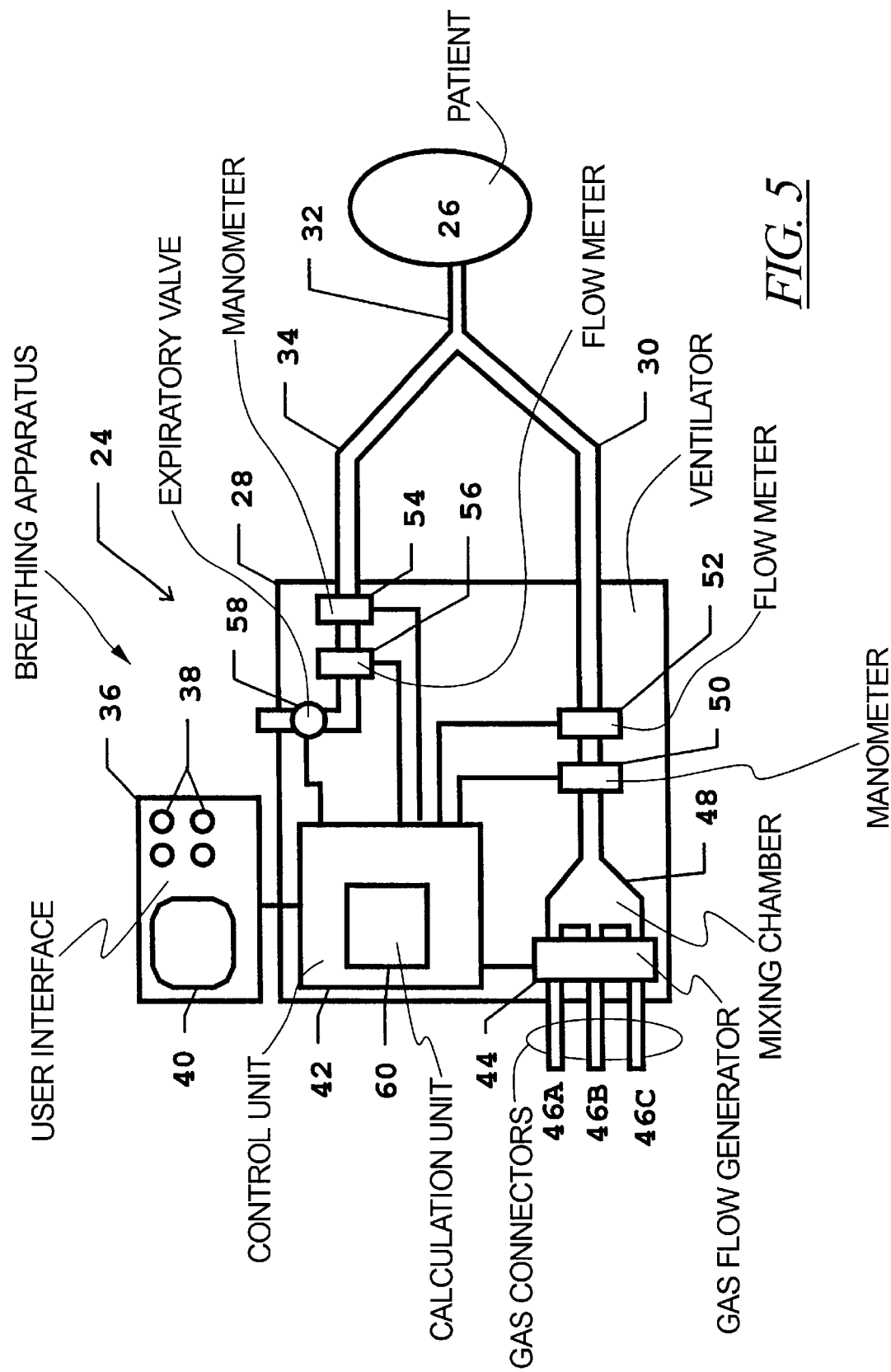
FIG. 5 is a block diagram of one embodiment of a breathing apparatus according to the invention.

FIG. 5 shows one embodiment of a breathing apparatus according to the invention. The breathing apparatus 24 can be connected to a patient 26 and provide her/him with breathing assistance. The breathing apparatus 24 includes a ventilator 28 which supplies breathing gas, via an inspiratory tube 30 and a patient tube 32, to the patient 26. Expired breathing gas is returned to the ventilator 28 through the patient tube 32 and an expiratory tube 34. The breathing apparatus 24 also has a user interface 36 which a physician can use for programming a suitable operating mode and breathing gas parameters for the ventilator 28 with the aid of control knobs 38. Visual information can be shown on a display 40. For example, the programmed operating mode of the ventilator 28 can be displayed as well as measured parameters such as flow, pressure, gas composition and the various parameters determined with the above-described methods according to the invention, i.e. Auto-PEEP, apparatus-PEEP, pressure gradient, extrapolation of the pressure gradient, the expiratory curve etc.

The user interface 36 can be integrated into the ventilator 28, or can communicate with it by wire, IR, radio waves or some other means. The user interface 36 communicates primarily with a control unit 42 in the ventilator 28. The control unit 42 controls all functions in the ventilator 28 and also collects all measurement values from meters, transducers and sensors in the ventilator 28 (or connected to the ventilator 28).

Breathing gas, in the form of one or more gases, is delivered to a first gas connector 46A, a second gas connector 46B and a third gas connector 46C. The flow and pressure of the connected gases (or gas) are regulated in a gas flow generator 44 and mixed into breathing gas in a mixing chamber 48 before being delivered to the patient 26 through an inspiratory tube 30. The pressure of breathing gas in the inspiratory part of the ventilator 28 can be measured by a first manometer 50, and flow can be measured by a first flow meter 52. (In principle, pressure and flow can also be obtained from the gas flow generator 48.)

Pressure on the expiratory side of the ventilator 28 can be determined by a second manometer 54, and flow can be determined by a second flow meter 56. An expiratory valve 58, controlled by the control unit 42, regulates the outflow of gas, apparatus-PEEP in particular.

A calculation unit 60 is arranged in the control unit 42. The calculation unit 60 is devised to perform the required signal analyses and calculations required for performing one or a plurality of the methods described above. In particular, the calculation unit 60 determines Auto-PEEP, pressure gradient, extrapolation calculations, delay calculations, inspiratory effort calculations and analysis of expiration curves.

The control unit 42 can also be modified to determine, from the various determinations the calculation unit 60 can perform, and propose on the display 40 possible changes in ventilator 28 settings. As an alternative, or complement, the control unit 42 can additionally be modified to automatically generate control and triggering signals related to the conditions ascertained by the calculation unit 60. Especially adaptation of the ventilator's 28 operating mode, as discussed above.

The magnitude of adaptations and the measure(s) that may be appropriate in any particular situation can be regulated in relation to compliance with certain pre-set conditions. Using an artificial neural network (ANN) or corresponding technology the control unit 42 can be successively "taught" to more reliably identify when a change in the operating mode is necessary and to more reliably propose the most advantageous change in operating mode.

The breathing apparatus has been described above as a ventilator, but the same arguments also pertain anaesthetic machines, respirators and other equipment for respiratory assistance.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining at least one parameter related to at least one of spontaneous attempts at inspiration by a patient connected to a breathing tube of a breathing apparatus and respiratory effort in spontaneous attempts at inspiration by a patient connected to a breathing tube of a breathing apparatus, comprising the steps of:

determining a pressure gradient relating a known apparatus pressure and time, said pressure gradient being generated by a patient connected to a breathing tube of a breathing apparatus upon inspiration;

determining a residual positive pressure in the lungs of a patient connected to a breathing tube of a breathing apparatus; and generating a signal dependent on said pressure gradient and said residual positive pressure.

2. A method as claimed in claim 1 wherein the step of determining a pressure gradient comprises determining said pressure gradient by extrapolation using said residual positive pressure, to obtain an extrapolated pressure gradient.

3. A method as claimed in claim 2 wherein said extrapolated pressure gradient has two intersections with said apparatus pressure, separated by a time delay, and comprising the additional steps of identifying said time delay and wherein the step of generating a signal includes generating a signal containing information regarding said time delay.

4. A method as claimed in claim 3 wherein said extrapolated pressure gradient and a curve representing said residual positive pressure enclose an area, and wherein said method includes the step of identifying said area, and wherein the step of generating a signal comprises generating a signal containing information regarding said area.

5. A method as claimed in claim 1 comprising the additional step of displaying a representation of said signal on a display.

6. A method for determining at least one parameter related to at least one of spontaneous attempts at inspiration by a patient connected to a breathing tube of a breathing apparatus and respiratory effort in spontaneous attempts at inspiration by a patient connected to a breathing tube of a breathing apparatus, comprising the steps of:

determining an expiratory curve for a patient connected to a breathing tube of a breathing apparatus for at least one breathing cycle; and extracting signal components relating to an attempt at inspiration by a patient connected to a breathing tube of a breathing apparatus from said expiratory curve.

7. A method as claimed in claim 6 comprising the additional steps of:

identifying an anticipated start of inspiration in a next attempt at inspiration by a patient connected to a breathing tube of a breathing apparatus after said one breathing cycle and, at said anticipated time, determining a pressure gradient relating a known apparatus pressure and time, said pressure gradient being generated by a patient connected to a breathing tube of a breathing apparatus upon inspiration, determining a residual positive pressure in the lungs of a patient connected to a breathing tube of a breathing apparatus, and generating a signal dependent on said pressure gradient and said residual positive pressure.

8. A method as claimed in claim 7 wherein the step of determining a pressure gradient comprises determining said pressure gradient by extrapolation using said residual positive pressure, to obtain an extrapolated pressure gradient.

9. A method as claimed in claim 8 wherein said extrapolated pressure gradient has two intersections with said apparatus pressure, separated by a time delay, and comprising the additional steps of identifying said time delay and wherein the step of generating a signal includes generating a signal containing information regarding said time delay.

10. A method as claimed in claim 8 wherein said extrapolated pressure gradient and a curve representing said residual positive pressure enclose an area, and wherein said method includes the step of identifying said area, and wherein the step of generating a signal comprises generating a signal containing information regarding said area.

11. A method as claimed in claim 7 comprising the additional step of displaying a representation of said signal on a display.

12. A breathing apparatus comprising:

a breathing tube adapted for connection to a patient, said patient at least occasionally breathing spontaneously;

a gas flow generator operably connected to said breathing tube for generating a gas flow of inspiratory gas therein for supply to a patient;

a first pressure meter operably connected to said breathing tube for identifying an inspiratory gas pressure;

a first flow meter operably connected to said breathing tube for identifying an inspiratory gas flow of;

a second pressure meter operably connected to said breathing tube for identifying a pressure of expiratory gas from a patient;

a second flow meter operably connected to said breathing tube for identifying a flow of said expiratory gas;

a control unit operably connected to each of said first and second pressure meters and each of said first and second flow meters for detecting inspiration attempts by a patient and operably connected to said gas flow generator for controlling said flow of inspiratory gas dependent on detection of said attempts at inspiration; and said control unit determining a pressure gradient in relation to a known apparatus pressure and time, said pressure gradient being generated by a patient at inspiration, and said control unit determining a residual positive pressure in the lungs of a patient, and said control unit generating a control signal for controlling said gas flow generator dependent on said pressure gradient and said residual positive pressure.

13. A breathing apparatus as claimed in claim 12 wherein said control unit obtains a value in said signal dependent on said pressure gradient and said residual positive pressure and compare said value with a predetermined value range and wherein said control unit controls said gas flow generator to generate an end expiratory apparatus pressure, consisting of a predetermined percentage of said residual positive pressure, if said value deviates from said value range.

14. A breathing apparatus as claimed in claim 12 wherein said control unit identifies a value in said signal dependent on said pressure gradient and said residual positive pressure and compare said value to a predetermined value range, and wherein said control unit calculates a change in at least one respiratory assistance parameter selected from the group consisting of inspiration duration, expiration duration, breathing gas flow, and title volume, if said value deviates from said value range.

15. A breathing apparatus comprising:

a breathing tube adapted for connection to a patient, said patient at least occasionally breathing spontaneously;

a gas flow generator operably connected to said breathing tube for generating a gas flow of inspiratory gas therein for supply to a patient;

a first pressure meter operably connected to said breathing tube for identifying an inspiratory gas pressure;

a first flow meter operably connected to said breathing tube for identifying an inspiratory gas flow;

a second pressure meter operably connected to said breathing tube for identifying a pressure of expiratory gas from a patient;

a second flow meter operably connected to said breathing tube for identifying a flow of expiratory gas from a patient;

a control unit connected to each of said first and second pressure meters and each of said first and second flow meters for detecting inspiration attempts by a patient and connected to said gas flow generator for controlling said flow of breathing gas dependent on detection of said attempts at inspiration; and said control unit determining an expiratory curve for one breathing cycle of a patient and extracting signal components from said expiratory curve related to an attempt at inspiration by a patient, and said control unit identifying an anticipated time of a next attempt at inspiration by a patient and, at said anticipated time, determining a pressure gradient in relation to a known apparatus pressure and time, said pressure gradient being generated by a patient at inspiration, and said control unit determining a residual positive pressure in the lungs of a patient, and said control unit generating a control signal for controlling said gas flow generator dependent on said pressure gradient and said residual positive pressure.

\* \* \* \* \*